(12) United States Patent
Dhingra et al.

(10) Patent No.: US 9,591,847 B2
(45) Date of Patent: Mar. 14, 2017

(54) CONTROL OF RIPENING AND SENESCENCE IN PRE-HARVEST AND POST-HARVEST PLANTS AND PLANT MATERIALS BY MANIPULATING ALTERNATIVE OXIDASE ACTIVITY

(71) Applicant: Washington State University, Pullman, WA (US)

(72) Inventors: Amit Dhingra, Pullman, WA (US); Christopher Hendrickson, Pullman, WA (US)

(73) Assignee: Washington State University, Pullman, WA (US)

(*) Notice: Subject to any disclaimer, the term of this patent is extended or adjusted under 35 U.S.C. 154(b) by 142 days.

(21) Appl. No.: 13/833,928

(22) Filed: Mar. 15, 2013

(65) Prior Publication Data

US 2014/0121110 A1 May 1, 2014

Related U.S. Application Data (60) Provisional application No. 61/719,859, filed on Oct. 29, 2012.

(51) Int. Cl.
| | | |
|---|---|---|
| *A01N 59/02* | (2006.01) | |
| *A01N 37/42* | (2006.01) | |
| *A01N 3/00* | (2006.01) | |
| *A23B 7/154* | (2006.01) | |

(52) U.S. Cl.
CPC ............... *A01N 3/00* (2013.01); *A01N 59/02* (2013.01); *A23B 7/154* (2013.01)

(58) Field of Classification Search
None
See application file for complete search history.

(56) References Cited

U.S. PATENT DOCUMENTS

| 5,972,840 A | 10/1999 | Mottram |
| 2006/0135369 A1 | 6/2006 | Beltran |

FOREIGN PATENT DOCUMENTS

| CN | 102550652 A | 7/2012 |
| WO | 2012/162335 A2 | 11/2012 |

OTHER PUBLICATIONS

Xu et al., 2012, Journal of Experimental Botany 63: 5705-5716.*
Polidoros et al., 2009, Physiologia Plantarum 137: 342-353.*
Vanlerberghe, 2013, Int. J. Mol. Sci. 14: 6805-6847.*
Considine et al., 2001, Plant Physiology 126: 1619-1629.*
Xiao et al., 2010, Zeitschrift für Naturforschung. Section C, Biosciences 65.7/8: 463-471.*
Watkins, 2006, Biotechnology Advances 24: 389-409.*
Duque and Arrabaca, 1999, Physiologia Plantarum 107: 24-31.*
Watkins, 2008, HortScience 43: 86-94.*
Fei Xu, et al., "The role of alternative oxidase in tomato fruit ripening and its regulatory interaction with ethylene", Journal of Experimental Botany, Jul. 16, 2012, pp. 5705-5716, vol. 63, No. 15.
David M. Rhoads and Lee McIntosh, "Salicylic Acid Regulation of Respiration in Higher Plants: Alternative Oxidase Expression", The Plant Cell, Sep. 1992, pp. 1131-1139, vol. 4, American Society of Plant Physiologists.

* cited by examiner

*Primary Examiner* — Amjad Abraham
*Assistant Examiner* — Bratislav Stankovic
(74) *Attorney, Agent, or Firm* — Christensen, O'Connor Johnson Kindness PLLC (57) ABSTRACT

Methods of controlling the maturation of plants and/or plant products (e.g. fruit, vegetable, ornamentals, etc.) by manipulating Alternative Oxidize (AOX) activity. An increase in activity hastens the maturation process while a decrease in activity slows or stops maturation.

6 Claims, 4 Drawing Sheets

Figure 6B

CONTROL OF RIPENING AND SENESCENCE IN PRE-HARVEST AND POST-HARVEST PLANTS AND PLANT MATERIALS BY MANIPULATING ALTERNATIVE OXIDASE ACTIVITY

CROSS-REFERENCE TO RELATED APPLICATIONS

This application claims benefit of U.S. provisional patent application 61/719,859, filed Oct. 29, 2012 the complete contents of which is hereby incorporated by reference.

STATEMENT OF FEDERALLY SPONSORED RESEARCH AND DEVELOPMENT

This invention was made, in part, with government support under Grant Nos. USDA 2009-31100-06053 awarded by the United States Department of Agriculture. The United States government has certain rights in the invention.

BACKGROUND OF THE INVENTION

Field of the Invention

The invention generally relates to methods of controlling the maturation of plants and plant materials. In particular, the invention provides methods to inactivate and activate Alternative Oxidase (AOX) gene expression in order to control the rate and timing of the maturation (e.g. ripening, senescence, etc.) of plants/plant products such as fruit, vegetables, ornamental plants, and other produce.

Background of the Invention

Climacteric fruit and cut flowers are typically treated with chemicals such as 1-methylcyclopropene (1-MCP) to block or slow down ripening and to extend storage and shelf-life. 1-MCP binds ethylene receptors blocking all downstream physiological and metabolic processes. Primarily, sensing of ethylene and subsequent signaling are blocked. While the use of 1-MCP has produced somewhat desirable results for some produce, its use has distinct drawbacks. For example, apples treated with 1-MCP remain desirable in terms of appearance, but they produce no or very limited amounts of volatile compounds, which reduces the fruit quality and desirability to consumers. The use of 1-MCP in some other fruits has been outright detrimental. For example, pears treated with 1-MCP do not ripen despite treatment with exogenous ethylene or the use of protocols intended to condition the fruit to ripen (e.g. various cold temperature treatments).

It would be desirable to have available methods of treating plants and plant materials (e.g. fruit, vegetables, ornamentals, etc.) so that they can be stored and shipped in an immature state (e.g. without ripening), and then readily matured at a desired time or within a desired time frame. It would be a boon to have available a method or mechanism to induce maturation of stored produce in a manner that results in the development of characteristics (e.g. softness, odor, aromas etc.) of produce that is allowed to mature naturally.

SUMMARY OF THE INVENTION

The alternative pathway respiration-related Alternative Oxidase (AOX) gene expression coincides with climacteric peak which is the hallmark of climacteric fruit (Duque and Arrabaca, 1999; Xu et al, 2012). However, prior to the present invention, the role of the enzyme as a controlling factor in plant maturation was not known. Experiments described herein have now shown that AOX gene expression is responsible for the physiological changes in plants and plant products which occur during ripening and senescence. Accordingly, the present invention provides methods to impact or influence expression of the AOX gene in order to slow or stop these processes, and/or to begin or resume the processes in a controlled, predictable manner.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

In some aspects, the invention provides methods of storing and subsequently maturing a plant or plant product. The methods comprise the steps of i) inactivating one or more Alternative Oxidase (AOX) genes in said plant or plant product; and, subsequently, ii) exposing said plant or plant product to an agent that activates said one or more AOX genes. Activation of the one or more AOX genes results in the onset of maturation of the plant/plant product. The step of inactivating may be carried out chemically or physiologically. If carried out chemically, this may be done by exposing the plant or plant product to 1-methylcyclopropene (1-MCP) or glycine betaine The agent that is applied may be applied as a gas or as a liquid. The agent may be applied by drenching, by spraying or by a slow release method. The agent may be or be applied with an antimicrobial. In some aspects, the step of inactivating is carried out physiologically by exposure to cold. The agent that activates at least one AOX gene is, for example, hydrogen sulfide, glyoxylic acid, salicylic acid, pyruvate, hydroxypyruvate, or a mixture of alanine and 2-oxoglutarate. The one or more AOX genes include AOX1 and AOX 2 or additional AOX gene family members. The plant or plant product may be, for example, a fruit, a vegetable, a tuberous root, a taproot, a bulb, a corm, a rhizome or a tuber, with exemplary fruits being pears, apples, bananas, avocadoes, and mangos; and exemplary vegetables being tomatoes and peppers. In some aspects, one or both of the steps of inactivating and exposing are carried out pre-harvest. In other aspects, one or both of the steps of inactivating and exposing are carried out post-harvest.

The invention also provides methods of overcoming blockage in ripening or senescence of a plant or plant product. The methods comprise a step of exposing the plant or plant product that has experienced a blockage in ripening or senescence to an agent that activates one or more Alternative Oxidase (AOX) genes. In some aspects, the agent is, for example, hydrogen sulfide, glyoxylic acid, salicylic acid, pyruvate, hydroxypyruvate, or a mixture of alanine and 2-oxoglutarate. The plant or plant product may be, for example, a fruit, a vegetable, a tuberous root, a taproot, a bulb, a corm, a rhizome or a tuber.

The invention also provides methods of hastening the maturation of an immature plant or plant product. The methods comprise a step of exposing the immature plant or plant product to an agent that activates one or more Alternative Oxidase (AOX) genes. In some aspects, the agent is, for example, hydrogen sulfide, glyoxylic acid, salicylic acid, pyruvate, hydroxypyruvate, or a mixture of alanine and 2-oxoglutarate. The plant or plant product may be, for example, a fruit, a vegetable, a tuberous root, a taproot, a bulb, a corm, a rhizome or a tuber.

DETAILED DESCRIPTION

In some aspects, the present invention exploits previously unknown properties of AOX enzymes in order to control or "time" plant/plant product maturation in a pathway-specific manner. In some aspects, the invention provides methods to control plant/plant product maturation, the methods including a step of first deactivating AOX (e.g. to induce cessation of or prevent or block onset of physiological or developmental changes which are characteristic of and/or which lead to ripening, senescence, etc.), and then, after a desired period of time, activating AOX to commence or recommence physiological/developmental changes which are characteristic of and/or which lead to maturation. In other aspects, methods to control plant/plant product maturation include only a step of activating AOX. The methods may be used pre- or post-harvest and in a variety of scenarios, as described in detail below. The following definitions apply throughout:

By "plants and/or plant products" or "plant materials" we mean photosynthetic, multicellular organisms of the kingdom Plantae including such groups as flowering plants, conifers, ferns and mosses; and/or products (e.g. reproductive and/or carbohydrate storage products) and parts thereof, e.g. leaves, blossoms, roots, stalks, stems, needles, fruit, seeds, buds, branches, bulbs, corms, rhizomes, and tubers. The "plants and/or plant products" may be pre-harvest (e.g. still attached to a tree, bush, etc. or still in the ground, or may be post-harvest, e.g. detached from a tree or bush, or extirpated from the ground or cleaved, cut or otherwise removed from a stalk, stem, vine, etc. The plants may or may not have been subject to prior post-harvest treatment(s) to control ripening. The plants may be processed e.g. slices or wedges or other portions of the plant may be treated, as may be packaged plants/plant products, and mixtures of plants/plant products. The plants may be climacteric or non-climacteric. Climacteric is a botanical term that indicates the period during which a plant part inclusive of the ones listed above exhibit a rise in the rate of respiration and release of ethylene at the time of ripening or maturing. Non-climacteric or aclimacteric plants are those that ripen without an increase in rate of respiration or release of ethylene.

By "AOX" gene or protein, we mean an alternative pathway respiration-related Alternative Oxidase (AOX) gene/protein. AOX is an enzyme that forms part of the electron transport chain in plants, as well as some fungi, protists and possibly some animals. The alternative oxidase is an integral membrane protein that is tightly bound to the inner mitochondrial membrane and which provides an alternative route for electrons passing through the electron transport chain to reduce oxygen. Since several proton-pumping steps are bypassed in this alternative pathway, activation of the oxidase reduces ATP generation. Particular examples of AOX genes include Pyrus communis AOX 1 and AOX 2 (PcAOX1 and PcAOX2). As used herein, "AOX" may refer to one AOX gene or protein, or may refer collectively to more than one AOX gene or protein.

By "maturation" as used herein, we mean the onset of physiological processes which lead to senescence in a plant or in plant material. In some cases (e.g. fruit), ripening occurs as a result of these processes. Other typical changes include ethylene release, changes in pigment and hence color, increase in sugars, changes in respiration, changes in soluble solids content, changes in titratable acidity, changes in fruit firmness, development of abscission zones, breakdown of cellular membranes, changes in the content of aromatic compounds etc.

Climacteric stage: For some fruits, a hallmark of entering into the maturation process is the climacteric stage, a stage of fruit ripening associated with ethylene production and cell respiration rise. Apples, bananas, melons, apricots, tomatoes (among others) are climacteric fruit. Climacteric is the final physiological process that marks the end of fruit maturation and the beginning of fruit senescence. Its defining point is the sudden rise in respiration of the fruit and normally takes place without any external influences. After the climacteric period, respiration rates (noted by carbon dioxide production) return to or below the point before the event. The climacteric event also leads to other changes in the fruit including (but not limited to) pigment changes and sugar release, flesh softening, release of aroma and titratable acidity. For those fruits raised as food the climacteric event marks the peak of edible ripeness, with fruits having the best taste and texture for consumption. After the event fruits are more susceptible to fungal invasion and begin to degrade with cell death.

The invention thus provides methods of inducing plants and/or plant products to exit or leave a state of active maturation, and/or to enter or re-enter a state of active maturation. In one embodiment, the plants/plant products are undergoing a maturation process and, according to methods of the invention, human intervention interrupts this process by inactivating AOX. The means of inactivating AOX may be, for example, imposing an environmental condition on the plant/plant product, or exposing the plant/plant product to (e.g. applying) an agent which has the effect of arresting maturation. Plants/plant products may thus be caused to remain in an immature, unripened state by any of several artificial (i.e. non-natural) means, including those which involve the manipulation of environmental conditions, and/or exposure of the plants/plant products to an agent which delays maturation, etc. Examples of the artificial manipulation of environmental conditions include but are not limited to: exposing the plants/plant products to cold, e.g. storing them at a temperature of less than about 15, 10, 5, 0, or −0.5° C.; preventing exposure to light, storage in modified atmospheres containing reduced amounts of respiration substrate, reduced amount of oxygen, increased amounts of nitrogen etc. Examples of agents that can be used to prevent or delay maturation include but are not limited to: 1-MCP (1-methylcyclopropene), AVG (aminoethoxyvinylglycine), and cytokinins (such as but not limited to zeatin, isopentyladenine, etc.). In addition, combinations of these may be used, e.g. plants/plant products may be stored in the cold and/or in the presence of one or more of such agents.

The plants/plant products in which an absence or decrease in AOX has been initiated (e.g. decreased below levels which would be present if measures directed to lowering the level of activity were not undertaken) generally do not actively undergo further physiological processes associated with maturation and/or ripening. Rather, the plants/plant products enter a quiescent or suspended state with respect to maturation. The plants/plant products may be referred to as arrested or suspended in an immature or pre-maturation state in which the normal or natural maturation pathway is blocked. Characteristics of such a state include but are not limited to: the plants/plant products do not produce ethylene or produce ethylene at a rate that is less than about 1-5 ul per kilogram plant products per hour (Song and Bangerth, 1996; Obando et al., 2007; Hoffman and Yang, 1980) respiration rates are low (e.g. $CO_2$ is be produced at a rate that is below about 1-15 ml per kilogram plant products per hour (Song and Bangerth, 1996; Ergun et al., 2005; Bower et al., 2002); for fruit, the BRIX score is less than about 5-15 Brix° (Trought and Bramley, 2011; Raffo et al., 2011; Sinha et al., 2012; Panarese et al., 2012) also for fruit, the level of firmness at or above about 5-15 lbf. (Palafox-Carlos et al., 2012; Sugar and Einhom, 2011). In addition, blockage may be detected by measuring the level of gene activity, e.g. by measuring AOX mRNA levels, protein levels and/or by measuring the amount or activity of the AOX enzyme, either directly or indirectly.

According to this method, the plants/plant products are released from this quiescent state by human intervention that induces AOX activity, also in an artificial, non-natural occurring manner, generally by exposure to an agent that activates AOX. By "induce AOX activity", we mean that one or more activities attributable to or characteristic of one or more AOX enzymes is induced, effected, increased, augmented, promoted, allowed or caused to proceed, released from inhibition, etc. For example, the ethylene production may occur or increase; respiration rates may increase; sugars may be released; changes in pigment may occur; firmness levels may decrease, etc.

In some aspects, the increase in AOX activity is the result of indirect activation (or reactivation) by turning on or increasing a level of AOX gene expression. Many agents can be used to activate (or reactivate) AOX gene expression. Exemplary agents include but are not limited to: hydrogen sulfide (Xiao et al., 2010); salicylic acid (Rhoads and McIntosh, 1992); pyruvate; hydroxypyruvate; glyoxylate; alanine plus 2-oxoglutarate (Pastore et al., 2001); acetylene (e.g. by application of purified calcium carbide), etc.

In other aspects, an increase in AOX activity is caused directly by activating the enzyme itself, e.g. via generation of a reducing environment (reduction of disulfide bonds within the AOX protein) with a suitable agent such as hydrogen sulfide similar to the methods described in U.S. Pat. No. 5,328,839 and U.S. Pat. No. 5,62,2132 (the complete contents of each of which are herein incorporated by reference) (also as European Patent EPO462674 A1), Umbach et al. (1994) and Perry et al. (1988). Activity of the AOX protein in vivo is thought to be dependent upon its oxidation-reduction state, with activity reported when protein subunits are reduced (Millenaar and Lambers, 2003; Umbach and Siedow, 1993). As a reducing agent, and potent inhibitor of cytochrome c oxidase, hydrogen sulfide (Millenaar and Lambers, 2003) may act in two ways to selectively partition electrons away from the terminus of the electron transport chain (ATP-synthase), and into the alternative oxidase pathway. The presence of a-ketoacids similarly stimulates AOX activity, such as those stated for use in this patent (Millenaar and Lambers, 2003), of which pyruvate, hydroxypyruvate are naturally produced in plant mitochondria at the site of the AOX protein.

The invention provides methods in which AOX activity is intentionally prevented, stopped or lessened at a desired time or point in maturation of a plants/plant material, and then the effects of this action are subsequently reversed at a later date (time) by intentionally exposing the plant/plant material to conditions and/or an agent that activates AOX in order to restart the maturation process. However, the invention also provides methods which involve only the former step or only the latter step are carried out. For example, the plants/plant products may not have been harvested and may not have yet undergone a "natural" ripening process in the field, orchard, etc., and it may be desirable to accelerate maturation on the tree or in the field by increasing AOX activity. This feature of the invention may be especially useful, for example, if different portions or sectors of a crop are ripening or expected to ripen at different rates, and if it would be desirable to hasten the process in the sector(s) that is/are slower so that the entire crop is at the same stage of readiness for harvest at the same time. Alternatively, AOX may be inactivated but only in discrete sectors of a crop which would otherwise mature sooner or earlier than desired, in order to allow other sectors to "catch up". Thus, the invention enables synchronization of production (e.g. maturation, harvest, etc.) of e.g. fruits, vegetables, and other plants. In addition, ripening may also be accelerated as need be to avoid crop loss, e.g. due to an impending, predicted weather untoward weather condition (e.g. low temperatures, frost, flooding, violent storms such as hurricanes, excessive precipitation [e.g. rain], etc.).

Other variants of the methods described herein may also be practiced. For example, one or both of the two steps of inactivation and activation of AOX may be used as necessary to coordinate, as desired, the stage(s) or level(s) of maturity of a crop. For example, maturation or the degree of maturation may be accelerated and/or slowed as needed so as to cause various sectors of a crop to ripen at different times, or to ripen at the same time, e.g. to accommodate the availability of harvesting equipment or personnel, or shipping or market conditions or constraints, or for fruit processing where fruit of equal maturity is desirable, etc. Activation can, for example, speed up ripening and senescence during pre-harvest stages.

The methods of the invention may be applied to any type of plant or plant material (e.g. fruit, vegetables, ornamental plants, etc.) for which it is desirable to control maturation. Thus, the terms "plant and plant material" as used herein are intended to be interpreted broadly, and to include plant-based agricultural products that are typically referred to as fruits, vegetables, grasses, grains, ornamental plants, bulbs, nuts, plant organs, seeds, etc.

With respect to fruit, those of skill in the art will recognize that the word "fruit" may have a variety of meanings. For example, standard definitions include: 1. edible part of plant: an edible part of a plant, usually fleshy and containing seeds; 2. ovary of a plant: the ripened seed-bearing ovary of a plant; and 3. produce: the produce of any plant grown or harvested by humans. In broad terms, "fruit" may refer to a structure of a plant that contains its seeds or a stone or pit. In non-technical usage, such as food preparation, "fruit" may refer to the fleshy seed-associated structures of certain plants that are sweet and edible in the raw state, such as apples, oranges, grapes, strawberries, juniper berries, bananas, etc., although non-sweet or less sweet fleshy structures (e.g. root vegetables such as carrots, beets, sweet potatoes, yams, etc.) are also included. Seed-associated structures that do not fit these informal criteria may be referred to by other names, such as vegetables, pods, ears, etc. In the botany of flowering plants, a "fruit" is a part that derives from specific tissues of the flower, mainly one or more ovaries. Taken strictly, this definition excludes many structures that are "fruits" in the common sense of the term, while including many structures that are not commonly called "fruits", such as bean or pea pods, corn kernels, tomatoes, etc. all of which are encompassed by the present invention.

Many fruits that, in a botanical sense, are true fruits are actually treated as vegetables in cooking and food preparation, including cucurbits (e.g., squash, pumpkin, gourds, melons, cucumbers, etc.), tomatoes, peas, beans, corn, eggplant, and sweet pepper, as wells as some spices, such as allspice and chilies.

As used herein, the term "fruit" refers to all plant products encompassed by the botanical, culinary and common meanings of the word.

Exemplary types of fleshy, simple fruits encompassed by the invention include but are not limited to: stone fruit or drupe (e.g. plum, cherry, peach, apricot, olive, mango, etc.); pome fruits of the family Rosaceae, (including apples, pears, rosehips, saskatoon berry, etc.);

aggregate fruits such as achenes (e.g. strawberry), follicles, drupelets (raspberry and blackberry), and various other berries; multiple fruits such as pineapple, fig, mulberry, osage-orange, breadfruit, hedge apple, etc; citrus fruits such as oranges, lemons limes, grapefruits, kumquats, tangelos, ugli fruit, tangerines, tangelos, minnolas, etc.; so-called "true" berries such as black current, red current, gooseberry, tomato, eggplant, guava, lucuma, chilis, pomegranates, kiwi fruit, grape, cranberry, blueberry, etc.; including both seeded and seedless varieties, as well as hybrid and genetically altered or manipulated varieties; and others such a avocados, persimmons, etc.

In one embodiment of the invention, the fruit that is treated using the methods and compositions of the invention is a pear. By "pear" we mean the fruit of a member of the genus Pyrus, examples of which include but are not limited to: *Pyrus amygdaliformis* (Almond-leafed pear); *Pyrus armeniacifolia; Pyrus boissieriana; Pyrus bourgaeana* (Iberian pear); *Pyrus×bretschneideri* (Chinese white pear; also classified as a subspecies of *Pyrus pyrifolia*); *Pyrus calleryana* (Callery pear); *Pyrus communis* (European pear); *Pyrus communis* subsp. *communis* (European pear cultivars of which include Beurre d'Anjou, Bartlett and Beurre Bosc); *Pyrus communis* subsp. *caucasica* (syn. *P. caucasica*); *Pyrus communis* subsp. *pyraster* (wild European pear (syn. *Pyrus pyraster*); *Pyrus cordata* (Plymouth pear); *Pyrus cossonii* (Algerian pear); *Pyrus dimorphophylla; Pyrus elaeagnifolia* (oleaster-leafed pear); *Pyrus fauriei; Pyrus gharbiana; Pyrus glabra; Pyrus hondoensis; Pyrus koehnei* (evergreen pear of southern China and Taiwan); *Pyrus korshinskyi; Pyrus mamorensis; Pyrus nivalis* (snow pear); *Pyrus pashia* (Afghan pear); *Pyrus xphaeocarpa; Pyrus pseudopashia; Pyrus pyrifolia* (Nashi pear, Sha Li); *Pyrus regelii; Pyrus salicifolia* (willow-leafed pear); *Pyrus×serrulata; Pyrus× sinkiangensis* (thought to be an interspecific hybrid between *P.×bretschneideri* and *Pyrus communis*); *Pyrus syriaca; Pyrus ussuriensis* (Siberian pear) and *Pyrus xerophila*.

Major types of pears which are marketed and which may be treated by the methods and compositions of the invention include but are not limited to: Williams' Bon Chrétien (sold in the United States. as Bartlett), Red Bartlett varieties, d'Anjou, Bosc, Comice, Concorde, and Seckel pears.

The methods of the invention may also be used to control the development, ripening, maturation or onset or progression of senescence of vegetables. As used herein, the term "vegetable" refers to an edible plant or part of a plant, and typically means the leaf, stem, or root of a plant but also includes some "fruits" as well (such as squash, see above). The meaning of this word is largely based on culinary and cultural tradition and all common meanings that are recognized by those of skill in the art are encompassed herein. Vegetables may be categorized as allium (e.g. onions, garlics, chives, leeks, etc.); brassica or cruciferous (e.g. cauliflower, cabbage, cress, bok choy, broccoli, mustards, mustard flowers, cauliflower, turnip, Chinese cabbage, rapeseed, radish, horseradish, arugula (rocket), Daikon radish, maca, Virginia pepperweed, wasabi, watercress etc.); composite (e.g. artichoke, chamomile, chicory, dandelion, endive, Jerusalem artichoke, lettuce, romaine, safflower, salsify, sunflower, etc.); gourds (e.g. cantaloupe, cucumber, melons, pumpkin, squash, watermelon, zucchini, etc.); umbelliferous (e.g. caraway, carrot, celery, cilantro, cumin, dill, fennel, parsley, parsnip, etc.); amaranth/goosefoot (e.g. amaranth, beet, chard, lamb's-quarters, quinoa, spinach, sugar beet, etc.); grass (e.g. bamboo shoots, sweet corn, wheatgrass, sugar cane, etc.); morning glory (e.g.

sweet potato, etc.); the yam family; nightshade (e.g. bell or sweet pepper, Italian pepper, chile pepper, eggplant, potato, tomato, tomatillo, and many spices, etc.); legumes (e.g. alfalfa, beans, carob, chickpea, green beans, jicama, lentil, pea, peanut, soy, etc.); mallow (e.g. cacao, cotton, okra, etc.); buckwheat family (e.g. buckwheat, garden sorrel, rhubarb, etc.); and others. Some vegetables are commonly referred to as "root" or "leafy green" vegetables, etc. All such vegetables may be treated using the methods and compositions of the invention.

The methods of the invention may also be used to control the development, maturation or senescence of ornamental plants and hence to preserve their freshness. As used herein, the phrase "ornamental plants" refers to plants that are grown for decorative purposes such as e.g., house plants, those grown for cut flowers, etc. as well as certain grasses, annuals, perennials, shrubs, trees, etc. As used herein the phrase has the same meaning that it is generally used in the horticultural trades.

Other facets of the invention include methods which advantageously exhibit a dual function in that some agents that block AOX activity or that induce AOX activity also have sterilizing properties. Thus, the invention also encompasses methods of simultaneously i) hastening maturation of a plant or plant product and ii) sterilizing the surface of the plant or plant product. The methods comprise a step of applying to a surface of the plant or plant product an agent that i) activates (or inactivates) Alternative Oxidase (AOX) activity and ii) possesses antimicrobial properties.

Application of the agents utilized in the methods may be carried out by any suitable means. Exemplary types of application include but are not limited to: gaseous application such as by fogging; application of a liquid, e.g. by drenching, dipping, spraying, etc. The agent may be in any form suitable for the selected method of application, e.g. as a solution, a solid (e.g. flakes, powder, etc.), in an emulsified form, in a chemically or physically encapsulated form etc. Further, the agents that control AOX activity may be applied alone, or in combination with each other, e.g. two or more agents may be combined. In addition, they may be applied with or without one or more other agents such as but not limited to: penetrants or adjuvants; or agents with other activities such as antimicrobials antifungals, coating materials (e.g. waxes, oils, etc.); antidessicants, etc. Further, delivery may be instantaneous (e.g. all at once during a single application), or by a slow release mechanism e.g. via slow release of a gas during storage in a closed chamber, or by a slow drip mechanism, etc. In addition, single applications may be repeated as necessary to achieve a desired effect, e.g. once per day or every few days for a designated period of weeks or months; or once per week for a designated period of weeks or months; or without a defined schedule as needed.

Plants/plant products treated according to the methods described herein are generally intended for consumption or use by humans. However, plants/plant products intended for consumption or use by animals are also encompassed. In some embodiments, the invention provides a plant/plant product that is treated by one or more of the methods described herein.

The following examples illustrate various embodiments of the invention but should not be interpreted so as to limit the invention in any way.

EXAMPLES

Example 1

As described for the first time herein, work in exemplary produce (pears) which were subjected to cold treatment to induce competency for ripening, has demonstrated that PcAOX1 and 2 (*Pyrus communis* Alternative Oxidase) expression correlates with the stage when 100% physiological competency for ripening is obtained.

Figure 1:
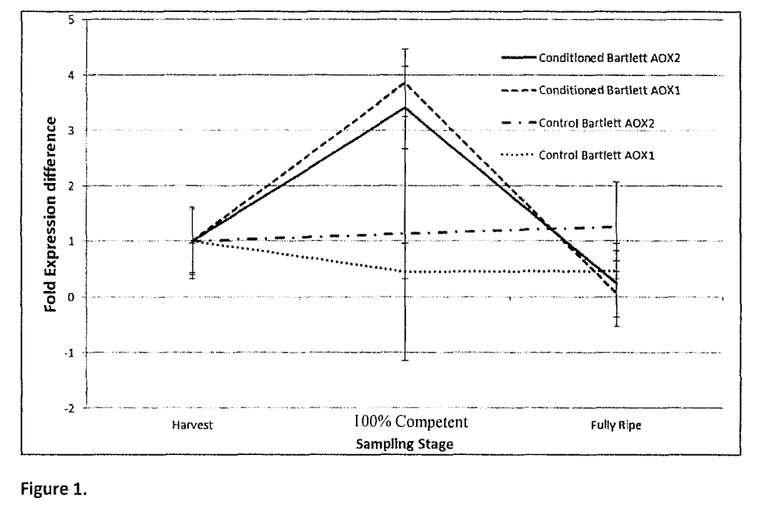
FIG. 1. Relative expression of alternative oxidase (PcAOX1, 2) expression in harvested, fully conditioned, and fully ripened pear fruit among 3 biological replicates. Ct-values were normalized to a control gene, 2-log transformed, then inverted. Error bars represent standard deviation. Compared to controls, AOX expression is 3 to 3.75 fold higher in conditioned fruit.

Analysis of PcAOX1 and 2 gene expression in ripening Bartlett pears compared to cold-conditioned pears was carried out by reverse transcription quantitative PCR The results are presented in FIG. 1. As can be seen, both PcAOX1 and PcAOX2 gene expression is activated 3.5 to 3.75-fold in ripening pears over the reference pears.

Bartlett pears were treated with i) 300 ppb of 1-MCP (Smartfresh) and ii) 0.5 and 2.5 mM $H_2S$ solution (RC-1), and iii) glyoxylic acid for 24 hours. Thereafter, each experimental group of fruit was placed in a separate air-tight chamber connected to a gas chromatography (GC) instrument configured to draw samples every 8 hours over the course of 5 days, to measure ethylene via a flame ionizing detector (FID), and to measure $CO_2$ via a gas analyzer. The experiment was performed with 4 pears per chamber in 3 replicates per experimental group. Monitoring was performed to detect minor variation in air flow rates in all experimental chambers used and detected variations were accounted for in subsequent calculations.

Figure 2:
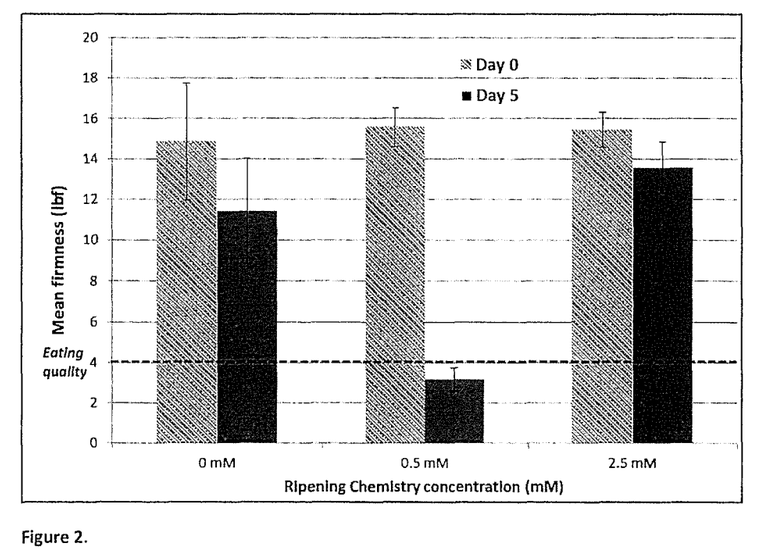
FIG. 2. Mean fruit firmness as calculated on day 0 and day 5. Note the drop in fruit firmness in fruit treated with 0.5 mM of Ripening compound-1 (RC-1) (dark bars). The firmness of 4 lbf and below represents eating quality in pear fruit.
Figure 3:
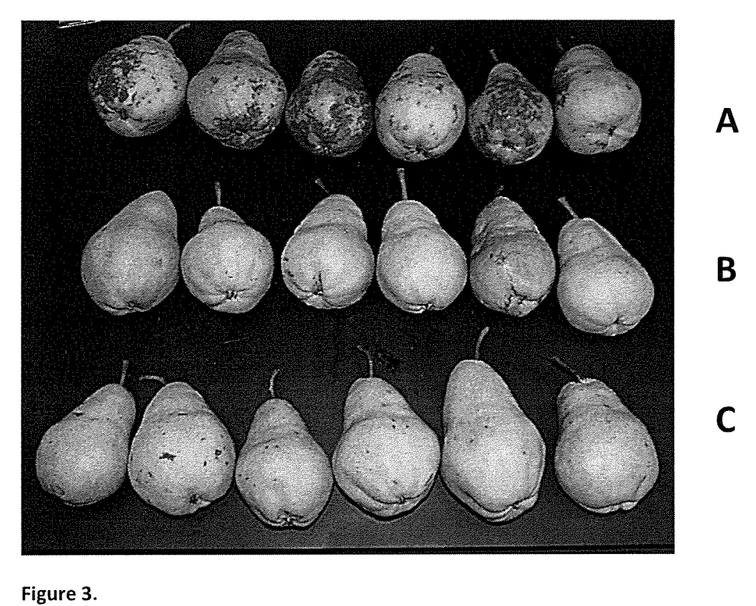
FIG. 3. Bartlett fruit treated with different concentrations of RC-1. Fruit treated with 0.5 mM of RC-1 (C) exhibited a loss of pigment compared to controls (B).

After 5 days of monitoring the fruit for ethylene and $CO_2$, fruit were sampled for flesh firmness and soluble solid content, measured in pounds of flesh firmness (lbf) and degrees Brix (respectively). The data were plotted and standard deviations were calculated.
Results
Firmness: Eating quality in pear fruit correlates to 4 lbf fruit firmness. Compared to control fruit, firmness of fruit treated with 0.5 mM of $H_2S$ (RC-1) dropped to 3.5 lbf (FIG. 2). In addition, it was noted that the $H_2S$-treated fruit lost its green pigmentation (FIG. 3). Interestingly, the higher dosage of $H_2S$ (2.5 mM) was ineffective and resulted in tissue damage.

Figure 4:
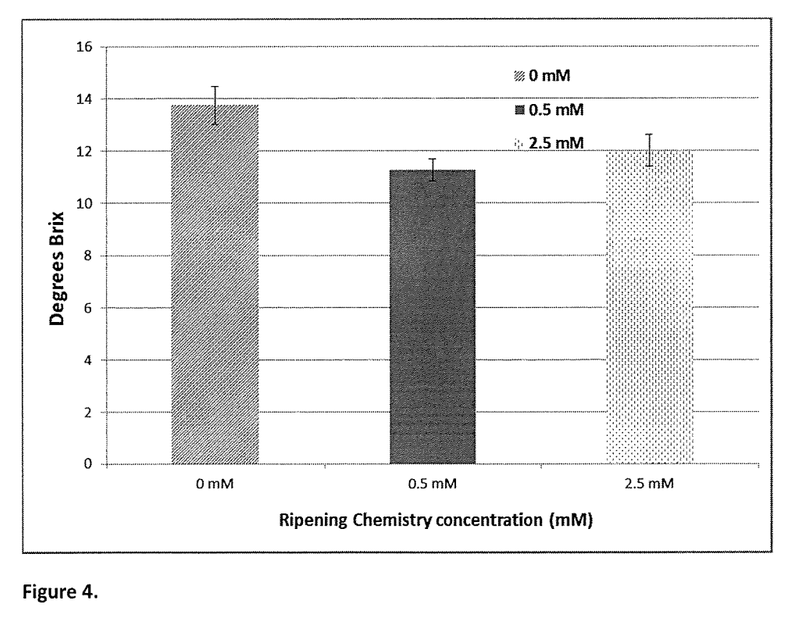
FIG. 4. Change in total soluble solids in fruit treated with RC-1.

Brix score: In the treated fruit, the Brix level, which is an indicator of fruit soluble solids, matched the range of desirable levels in commercial fruit (FIG. 4).

Figure 5:
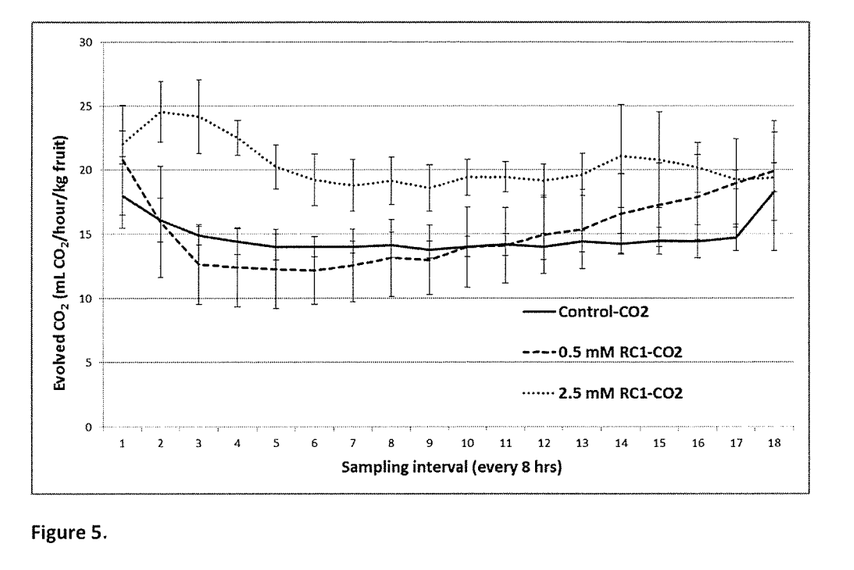
FIG. 5. Evolved $CO_2$ measured in ml per hour per kilogram of fruit. Note the positive trend in fruit treated with 0.5 mM of RC-1.

Carbon dioxide: The level of respiration (as indicated by $CO_2$ levels) in pears treated with 0.5 mM $H_2S$ showed a generally positive trend (FIG. 5) ultimately surpassing the levels observed in fruit treated with 2.5 mM $H_2S$, which showed higher levels of carbon dioxide, perhaps as a stress response. This stress manifests itself in damaged tissues that are visible in FIG. 4. In untreated fruit, the levels of $CO_2$ remained constant.

Figure 6A:
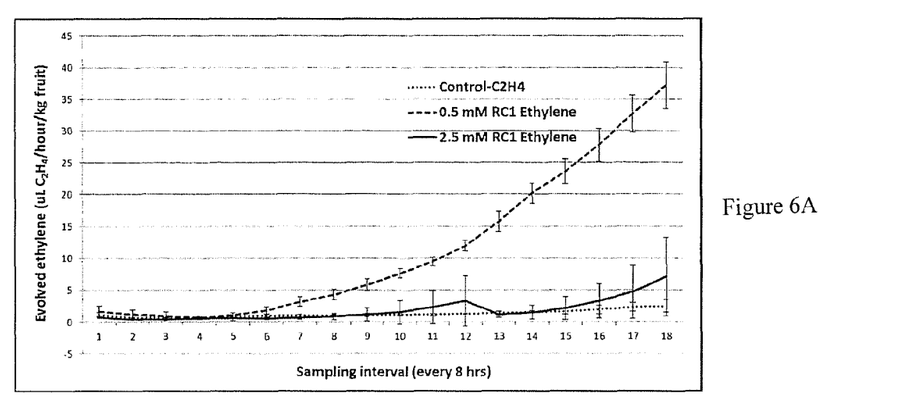
FIGS. 6A and B. Evolution of ethylene measured in microliter per hour per kilogram fruit in per fruit blocked for ripening by 1-MCP. A, effects of exposure to RC-1: ethylene evolution is observed 48 hrs post-treatment with RC-1; B, effects of exposure to of Ripening compound-2 (RC-2): at 0.25 mM of RC-2 ethylene evolution is observed within 16 hrs.

Ethylene: The most important characteristic of fruit during climacteric or ripening is release of ethylene. Ethylene production was measured as microliters of ethylene per hour per kilogram of fruit. The level of ethylene in the control fruit and fruit treated with 2.5 mM of $H_2S$ (FIG. 6A or with 1, 2.5 and 10 mM of $H_2S$ (FIG. 6B) remained indistinguishable and very low.

Figure 6B:
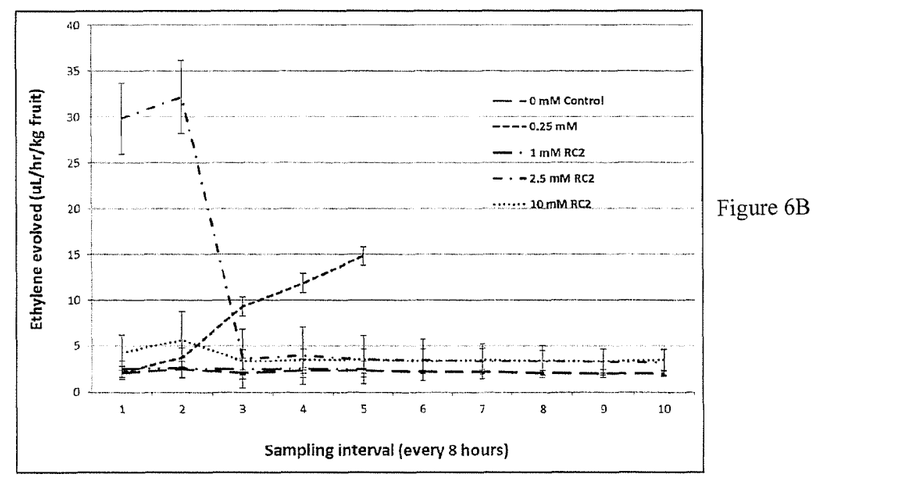

However, in the fruit treated with 0.5 mM of $H_2S$ and 0.25 mM glyoxylic acid (RC-2), a clear and steady increase in the evolution of ethylene was observed (FIGS. 6A and B), correlating well with the decrease in fruit firmness and concomitant change in the amount of total soluble solids, and demonstrating the effectiveness of this approach to the induction of ripening.

REFERENCES

Song, J., and Bangerth, F. 1996. The effect of harvest date on aroma compound production from 'Golden Delicious' apple fruit and relationship to respiration and ethylene production. Postharvest Biol. and Technol. 8, 259-269.

Ramina, A., Chang, C., Giovannoni, J., Klee, H., Perata, P., Woltering, E. (eds.)., Advances in Plant Ethylene Research: Proceedings of the 7$^{th}$ International Symposium on the Plant Hormone Ethylene, 197-205. 2007. Springer.

Hoffman, N. E., and S. F. Yang. 1980. Changes of 1-aminocyclopropane-1-carboxylic acid content in ripening fruits in relation to their ethylene production rates. J. Am. Soc. Hort. Sci. 105 (4):492-495.

Ergun, M., Jeong, J., Huber, D. J., and Cantliffe, D. J. 2005. Suppression of ripening and softening of 'Galia' melons by 1-methylcyclopropene applied at preripe or ripe stages of development. HortSci. 40 (1), 170-175.

Bower, J., Holford, P., Latch, A., Pech, J. 2002. Culture conditions and detachment of the fruit influence the effect of ethylene on the climacteric respiration of melon. Postharvest Biol. and Technol. 26 (2), 135-146.

Trought, M. C. T., and Bramley, R. G. V. 2011. Vineyard variability in Marlborough, New Zealand: characterising spatial and temporal changes in fruit composition and juice quality in the vineyard. Australian J. Grape and Wine Res. 17 (1), 79-89.

Raffo, M. D., Candan, A. P., De Angelis, V., Mañeco, L., Miranda, M. J., and Barda, N. 2011. Sensory evaluation of pears: a useful tool to detect changes in eating quality during ripening. Acta Hort. 909, 651-656.

Sinha, N., Sidhu, J., Barta, J., Wu, J., and Cano, M. P. (eds.)., Handbook of Fruits and Fruit Processing, 369-375. 2012. John Wiley & Sons.

Panarese, V., Tylewicz, U., Santagapita, P., Rocculi, P., Rosa, M.D. 2012. Isothermal and differential scanning calorimetries to evaluate structural and metabolic alterations of osmo-dehydrated kiwifruit as a function of ripening stage. Innov. Food Sci. and Emerging Technol. 15, 66-71.

Palafox-Carlos, H., Yahia, E., Islas-Osuna, M. A., Gutierrez-Martinez, P., Robles-Sánchez, M., González-Aguilar, G. A. 2012. Effect of ripeness stage of mango fruit (Mangifera indica L., cv. Ataulfo) on physiological parameters and antioxidant activity. Scientia Hortic. 135,7-13.

Sugar, D., and Einhom, T. C. 2011. Conditioning temperature and harvest maturity influence induction of ripening capacity in 'd'Anjou' pear fruit. Postharvest Biol.and Technol. 60 (2), 121-124.

Duque, P., and Arrabaca, J. D. (1999) Respiratory metabolism during cold storage of apple fruit. II. Alternative oxidase is induced at the climacteric. Physiologia Plantarum, 107 (1), 24-31.

Umbach, A. L., Wiskich, J. T., and Siedow, J. N. 1994. Regulation of alternative oxidase kinetics by pyruvate and intermolecular disulfide bond redox status in soybean seedling mitochondria. FEBS Letters. 348 (2),181-184.

Perry, D., Abraham, E. P., and Baldwin, J. E. 1988. Factors affecting the isopenicillin N synthetase reaction. Biochem. J. 255 (1), 345-351.

Millenaar, F. F., and Lambers, H. 2003. The Alternative Oxidase: in vivo regulation and function. Plant Biol. 5 (1), 2-15.

Umbach, A. L., and Siedow, J. N. 1993. Covalent and noncovalent dimers of the cyanide-resistant alternative oxidase protein in higher plant mitochondria and their relationship to enzyme activity. Plant Physiol. 103, 845-854.

Pastore, D., Trono, D., Laus, M. N., Di Fonzo, N., and Passarella, S. (2001) Alternative oxidase in durum wheat mitochondria. Activation by pyruvate, hydroxypyruvate and glyoxylate and physiological role. Plant and Cell Physiology, 42 (12), 1373-1382.

Rhoads, D. M., and Mcintosh, L. (1992) Salicylic-Acid Regulation of Respiration in Higher-Plants—Alternative Oxidase Expression. Plant Cell, 4 (9), 1131-1139.

Xiao, M., Ma, J., Li, H. Y., Jin, H., and Feng, H. Q. (2010) Effects of Hydrogen Sulfide on Alternative Pathway Respiration and Induction of Alternative Oxidase Gene Expression in Rice Suspension Cells. Zeitschrift Fur Naturforschung Section C—a Journal of Biosciences, 65 (7-8), 463-471.

Xu, F., Yuan, S., Zhang, D. W., Lv, X., and Lin, H. H. (2012) The role of alternative oxidase in tomato fruit ripening and its regulatory interaction with ethylene. J Exp Bot, 63 (15), 5705-5716.

All references cited herein, including patents and patent applications, are hereby incorporated by reference in entirety.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of storing and subsequently maturing a pear, said method comprising
    exposing said pear to 1-methylcyclopropene (1-MCP) sufficient to arrest maturation of said pear; and, subsequently,
    exposing said pear to 0.5 mM or less hydrogen sulfide, wherein the exposure to said hydrogen sulfide results in maturation of said pear evidenced by evolution of ethylene in an amount greater than in the absence of hydrogen sulfide exposure.

2. The method of claim 1, wherein said hydrogen sulfide is applied as a gas or as a liquid.

3. The method of claim 1, wherein said hydrogen sulfide is applied by drenching, by spraying or by a slow release method.

4. The method of claim 1, wherein one or both of said steps of exposing are carried out under pre-harvest conditions.

5. The method of claim 1, wherein one or both of said steps of exposing are carried out under post-harvest conditions.

6. The method of claim 1, further comprising a step of cutting or slicing said pears after said first exposing step and before said second exposing step.

* * * * *